(12) United States Patent
Tishkov et al.

(10) Patent No.: US 8,541,612 B2
(45) Date of Patent: Sep. 24, 2013

(54) UNSATURATED DIPHOSPHINE MONOXIDES

(75) Inventors: Alexander Tishkov, Moskau (RU);
Klemens Massonne, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 438 days.

(21) Appl. No.: 12/921,298

(22) PCT Filed: Mar. 23, 2009

(86) PCT No.: PCT/EP2009/053339
§ 371 (c)(1),
(2), (4) Date: Sep. 7, 2010

(87) PCT Pub. No.: WO2009/121736
PCT Pub. Date: Oct. 8, 2009

(65) Prior Publication Data
US 2011/0034734 A1    Feb. 10, 2011

(30) Foreign Application Priority Data

Apr. 1, 2008   (EP) ..................................... 08153886

(51) Int. Cl.
*C07F 9/141* (2006.01)

(52) U.S. Cl.
USPC .............................. 558/155; 558/157; 568/14

(58) Field of Classification Search
USPC ................... 558/155, 157; 568/14
See application file for complete search history.

(56) References Cited

U.S. PATENT DOCUMENTS

2010/0137643 A1   6/2010   Tishkov et al.
2011/0190407 A1*  8/2011   Balbo Block et al. ......... 521/108

FOREIGN PATENT DOCUMENTS

WO        2005 103136     11/2005

OTHER PUBLICATIONS

Chen Z. et al, Chemistry European Journal, 2001, 7, 20, 4447-4455.*
Teo T. et al, Inorganica Chimica Acta 352 (2003), 213-219.*
International Preliminary Report on Patentability issued Jun. 28, 2010 in PCT/EP09/053339 filed Mar. 23, 2009.
International Search Report issued Jul. 29, 2009 in PCT/EP09/053339 filed Mar. 23, 2009.
Foss, V. L. et al., "Effect of Steric Hindrances on the Relative Thermodynamic Stability of Trialkylalkoxydiphosphine Monoxides and Their Isomeric Anhydrides", Zhurnal Obshchei Khimii, vol. 53, No. 10, database accession No. 1984:103467, ISSN: 0044-460X, XP002532591, (1983) (English abstract only).
Foss, V. L. et al., "Interconversion of Monoxides of Symmetric Dialkyldialkoxydiphosphines and Their Isomeric Anhydrides", Zhurnal Obshchei Khimii, vol. 49, No. 11, database accession No. 1980:128147, ISSN: 0044-460X, XP002532592, (1979) (English abstract only).
Lutsenko, I. F. et al., "Rearrangements of Diphosphine Oxides and Anhydrides of Phosphorus Acids, Phosphorotropic Tautomerism", Pure and Applied Chemistry, vol. 52, No. 4, pp. 917-944, XP 009118342 ISSN: 0033-4545 (1980).
Ruflin, C. et al., "Tetrakis (trimethysilyl) Hypophosphate $P_2O_2(OTMS)_4$: Synthesis, Reactivity and Application as Flame Retardant", Heteroatom Chemistry, vol. 18, No. 7, pp. 721-731, ISSN: 1042-7163, XP009118331 (2007).
Massone, Ch. et al., "Polycations. Part 16. Polyphosphonium Species Containing Phosphorus-Phosphorus Bonds", Polish Journal of Chemistry, vol. 79, No. 3, pp. 481-485 ISSN:0137-5083, XP 009118344 (2005).
Fluck, E. et al., "Darstellung Von Verbindungen Mit P-P-Und P-P-P—Gerusten", Inorg. Nucl. Chem. Letters, vol. 3, No. 8, pp. 307-313, (1967).

* cited by examiner

*Primary Examiner* — Johann R Richter
*Assistant Examiner* — Pancham Bakshi
(74) *Attorney, Agent, or Firm* — Oblon, Spivak, McClelland, Maier & Neustadt, L.L.P.

(57) ABSTRACT

The present invention relates to unsaturated diphosphine monoxides, to a process for preparation thereof and to the use thereof as flame retardants.

6 Claims, No Drawings

UNSATURATED DIPHOSPHINE MONOXIDES

The present invention relates to unsaturated diphosphine monoxides, to a process for preparation thereof and to the use thereof as flame retardants.

There is a drive to replace halogenated flame retardants with corresponding halogen-free flame retardants. It is particularly advantageous when the flame retardant can be mixed not just physically into the material to be protected, but also bonds to its structure and thus cannot be removed from the material by physical processes. There is a great need for unsaturated diphosphine monoxides which can also be incorporated into polymerizable plastics as flame retardants. The present application describes the diphosphine monoxides which comprise unsaturated C—C bonds.

Inorg. Nucl. Chem. Letters, 1967, Vol. 3, on page 313, describes the reaction of dialkyl- or diphenylphosphine chloride with trimethoxyphosphine or with methoxydiphenylphosphine to give the corresponding diphosphine monoxide according to the scheme below.

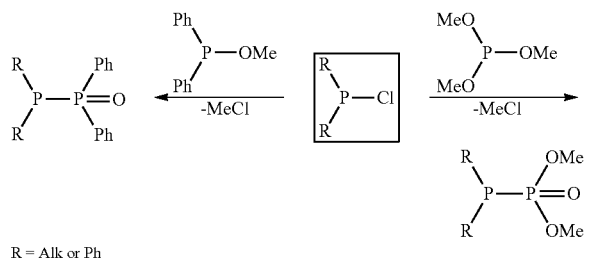

R = Alk or Ph

The disadvantage of the obtainable dialkoxy derivatives and of tetraphenyldiphosphine monoxide is that they cannot be incorporated chemically into the polymerizable network of the plastic.

It is therefore an object of the present invention to provide compounds which are firstly halogen-free, secondly can be incorporated chemically into a polymer matrix and thirdly have outstanding flame retardancy properties.

This object is achieved by compounds of the formula I

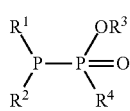

where the R1-R2 radicals are each independently selected from the group of $C_1$-$C_{16}$-alkyl, $C_1$-$C_{16}$-alkenyl, $C_1$-$C_{16}$-alkoxy, $C_1$-$C_{16}$-alkenyloxy, $C_3$-$C_{10}$-cycloalkyl, $C_3$-$C_{10}$-cycloalkoxy, $C_6$-$C_{10}$-aryl, $C_6$-$C_{10}$-aryloxy, $C_6$-$C_{10}$-aryl-$C_1$-$C_{16}$-alkyl, $C_6$-$C_{10}$-aryl-$C_1$-$C_{16}$-alkoxy, $NR^2R^3$, $COR^2$, $COOR^2$ and $CONR^2R^3$, the $R^3$ radical is a substituted or unsubstituted, heteroatom-comprising or non-heteroatom-comprising, organic hydrocarbon group which comprises at least one double bond, and $R^4$ is selected from the group of $C_1$-$C_{16}$-alkyl, $C_1$-$C_{16}$-alkenyl, $C_1$-$C_{16}$-alkenyloxy, $C_1$-$C_{16}$-alkoxy, $C_1$-$C_{16}$-alkyl-$NR^2R^3$, $C_3$-$C_{10}$-cycloalkyl, $C_3$-$C_{10}$-cycloalkoxy, $C_6$-$C_{10}$-aryl, $C_6$-$C_{10}$-aryloxy, $C_6$-$C_{10}$-aryl-$C_1$-$C_{16}$-alkyl, $C_6$-$C_{10}$-aryl-$C_1$-$C_{16}$-alkoxy, $NR^2R^3$, $COR^2$, $COOR^2$ and $CONR^2R^3$, preference being given to $C_1$-$C_{16}$-alkyl and $C_6$-$C_{10}$-aryl groups.

The inventive compounds are advantageous when $OR^3$ and $R^4$ in the compound of the formula I are identical.

The inventive compounds are advantageous when $R^3$ and $R^4$ in the compound of the formula I are allyloxy groups.

The present invention further provides a process for preparing the compounds of the formula I according to any one of claims 1 to 3, comprising the following steps a) reacting a compound of the formula II

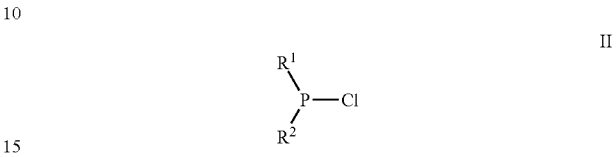

b) with the compound of the formula III

where the $R^5$ radical is selected from the group of $C_1$-$C_{16}$-alkyl, $C_1$-$C_{16}$-alkenyl, $C_3$-$C_{10}$-cycloalkyl and $C_6$-$C_{10}$-aryl.

The process according to the invention is advantageous when the reaction of the compound of the formula II with the compound of the formula III is carried out at temperatures of from 0° C. to 150° C.

The invention further provides for the use of the compounds of the formula I as flame retardants in plastics.

The $R^1$-$R^2$ radicals are each independently selected from the group of $C_1$-$C_{16}$-alkyl, $C_1$-$C_{16}$-alkenyl, $C_1$-$C_{16}$-alkoxy, $C_1$-$C_{16}$-alkenyloxy, $C_3$-$C_{10}$-cycloalkyl, $C_3$-$C_{10}$-cycloalkoxy, $C_6$-$C_{10}$-aryl, $C_6$-$C_{10}$-aryloxy, $C_6$-$C_{10}$-aryl-$C_1$-$C_{16}$-alkyl, $C_6$-$C_{10}$-aryl-$C_1$-$C_{16}$-alkoxy, $NR^2R^3$, $COR^2$, $COOR^2$ and $CONR^2R^3$. Preferred $C_1$-$C_{16}$-alkyl groups are methyl, ethyl, n-propyl, i-propyl, n-butyl, tert-butyl, i-butyl, hexyl, octyl, decyl, dodecyl, tetradecyl, 2-ethylhexyl and 2-propylheptyl.

Preferred $C_6$-$C_{10}$-aryl groups are phenyl and naphthyl. Particular preference is given to phenyl.

It is very particularly preferred when the $R^1$ and $R^2$ radicals are identical. The phenyl group is very especially preferred for $R^1$ and $R^2$.

The $R^3$ radical is a substituted or unsubstituted, heteroatom-comprising or non-heteroatom-comprising, organic hydrocarbon group which comprises at least one double bond. $R^3$ is preferably selected from the group of vinyl, allyl, 2-vinyloxyethyl, 2-vinyloxyethyloxyethyl and other ethoxylated oligomers. The allyl group is very particularly preferred for $R^3$.

The $R^4$ radical is selected from the group of $C_1$-$C_{16}$-alkyl, $C_1$-$C_{16}$-alkenyl, $C_1$-$C_{16}$-alkenyloxy, $C_1$-$C_{16}$-alkoxy, $C_1$-$C_{16}$-alkyl-$NR^2R^3$, $C_3$-$C_{10}$-cycloalkyl, $C_3$-$C_{10}$-cycloalkoxy, $C_6$-$C_{10}$-aryl, $C_6$-$C_{10}$-aryloxy, $C_6$-$C_{10}$-aryl-$C_1$-$C_{16}$-alkyl, $C_6$-$C_{10}$-aryl-$C_1$-$C_{16}$-alkoxy, $NR^2R^3$, $COR^2$, $COOR^2$ and $CONR^2R^3$, preference being given to $C_1$-$C_{16}$-alkyl and $C_6$-$C_{10}$-aryl groups.

Particularly preferred compounds are those in which the $R^1$ and $R^2$ radicals and the $OR^3$ and $R^4$ radicals are identical. Very particular preference is given to compounds in which $R^1$ and $R^2$ are each $C_6$-$C_{10}$ aryl groups, especially phenyl groups, and $OR^3$ and $R^4$ are each alkenyloxy groups, especially allyloxy groups.

The $R^5$ radical in the process according to the invention is identical to $R^1$, $R^2$, $R^3$ or $R^4$. $R^5$ is preferably identical to $R^3$. Allyl is especially preferred.

The inventive compounds of the formula I are prepared by reacting the compounds of the formula II with those of the formula III.

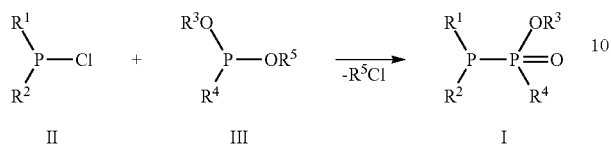

The reaction of the compounds of the formula II with III can be carried out in the presence of solvents. Preferred solvents are aromatic solvents selected from the group of toluene, xylene and mesitylene. The reaction is performed preferably at temperatures in the range from 0 to 150° C., more preferably in the range from 20 to 120° C. and most preferably in the range from 20 to 30° C. The solvent is removed after the reaction has ended. The solvent can be removed by any method of removal known to those skilled in the art. Preference is given to distilling. The resulting product is then dried. Preference is given to drying under a reduced pressure in the range from 300 to 3 mbar.

The resulting product can be used as a flame retardant in different plastics, by virtue of the inventive product being bound to the polymeric backbone by copolymerization or blended with the plastic by compounding.

EXAMPLE

Preparation of 1,1-diphenyl-2,2-diallyloxydiphosphine monoxide

Triallyl phosphite (101 g, 0.5 mol) in toluene (500 ml) is initially charged in a round bottom flask. Within 1 h, chlorodiphenylphosphine (110.5 g, 0.5 mol) is added dropwise at 25° C. The mixture is stirred under reflux for a further 7 hours and then cooled. Toluene is distilled off over a Claisen apparatus at 60° C. and 1 mbar. The product is dried under oil-pump vacuum. The product (147 g, 85% yield) is obtained as a clear yellow liquid of purity>80% ($^{31}P$ NMR). $^{31}P$ NMR (toluene-D8): −31.1 (d, $^1J$ 204 Hz); 34.1 (d, $^1J$ 204 Hz).

The invention claimed is:

1. A compound of the formula I

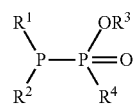

where the R1-R2 radicals are each independently selected from the group consisting of $C_1$-$C_{16}$-alkyl, $C_1$-$C_{16}$-alkenyl, $C_1$-$C_{16}$-alkoxy, $C_1$-$C_{16}$-alkenyloxy, $C_3$-$C_{10}$-cycloalkyl, $C_3$-$C_{10}$-cycloalkoxy, $C_6$-$C_{10}$-aryl, $C_6$-$C_{10}$-aryloxy, $C_6$-$C_{10}$-aryl-$C_1$-$C_{16}$-alkoxy, $NR^2R3$, $COR^2$, $COOR^2$ and $CONR^2R^3$, the $R^3$ radical is an allyl group and $R^4$ is an allyloxy group.

2. A process for preparing the compounds of the formula 1 according to claim 1, comprising
a) reacting a compound of the formula II

b) with the compound of the formula III

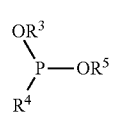

where the $R^5$ radical is selected from the group consisting of $C_1$-$C_{16}$-alkyl, $C_1$-$C_{16}$-alkenyl, $C_3$-$C_{10}$-cycloalkyl and $C_6$-$C_{10}$-aryl.

3. The process according to claim 2, wherein the reaction of the compound of the formula II with the compound of the formula III is carried out at temperatures of from 0° C. to 150° C.

4. A flame retardant, comprising the compound of formula I according to claim 1.

5. The compound of claim 1, wherein $R^1$ and $R^2$ are phenyl.

6. The flame retardant according to claim 4, which is suitable as a flame retardant in plastics.

* * * * *